US008097020B2

(12) United States Patent
Markworth et al.

(10) Patent No.: US 8,097,020 B2
(45) Date of Patent: Jan. 17, 2012

(54) PEDICLE DYNAMIC FACET ARTHROPLASTY SYSTEM AND METHOD

(75) Inventors: Aaron D. Markworth, Saddle Brook, NJ (US); Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 1007 days.

(21) Appl. No.: 11/608,856

(22) Filed: Dec. 11, 2006

(65) Prior Publication Data

US 2008/0140134 A1 Jun. 12, 2008

Related U.S. Application Data

(63) Continuation-in-part of application No. 11/045,908, filed on Jan. 28, 2005, now Pat. No. 7,862,594.

(60) Provisional application No. 60/548,543, filed on Feb. 27, 2004, provisional application No. 60/565,658, filed on Apr. 27, 2004.

(51) Int. Cl.
*A61B 17/70* (2006.01)
(52) U.S. Cl. ........................................................ 606/247
(58) Field of Classification Search ........... 606/247–279
See application file for complete search history.

(56) References Cited

U.S. PATENT DOCUMENTS

| | | | |
|---|---|---|---|
| 3,054,321 A | 9/1962 | Macchia | |
| 5,735,851 A | 4/1998 | Errico et al. | |
| 5,752,957 A | 5/1998 | Ralph et al. | |
| 5,989,250 A | 11/1999 | Wagner et al. | |
| 6,030,389 A | 2/2000 | Wagner et al. | |
| 6,214,049 B1* | 4/2001 | Gayer et al. | 623/16.11 |
| 6,554,834 B1 | 4/2003 | Crozet et al. | |
| 6,811,567 B2 | 11/2004 | Reiley | |
| 6,890,334 B2 | 5/2005 | Brace et al. | |
| 6,974,478 B2 | 12/2005 | Reiley et al. | |
| 7,041,136 B2 | 5/2006 | Goble et al. | |
| 7,074,237 B2 | 7/2006 | Goble et al. | |
| 7,087,084 B2 | 8/2006 | Reiley | |
| 7,090,698 B2 | 8/2006 | Goble et al. | |
| 7,524,326 B2 | 4/2009 | Dierks | |
| 2003/0100896 A1* | 5/2003 | Biedermann et al. | 606/61 |
| 2003/0163133 A1 | 8/2003 | Altarac et al. | |
| 2005/0131409 A1 | 6/2005 | Chervitz et al. | |
| 2005/0192571 A1 | 9/2005 | Abdelgany | |
| 2005/0192572 A1 | 9/2005 | Abdelgany et al. | |
| 2005/0192573 A1 | 9/2005 | Abdelgany et al. | |
| 2005/0203518 A1 | 9/2005 | Biedermann et al. | |
| 2006/0161152 A1 | 7/2006 | Ensign et al. | |
| 2007/0093831 A1* | 4/2007 | Abdelgany et al. | 606/61 |

FOREIGN PATENT DOCUMENTS

DE 19950075 4/2001
* cited by examiner

*Primary Examiner* — Eduardo C Robert
*Assistant Examiner* — Summer Kostelnik
(74) *Attorney, Agent, or Firm* — Rahman LLC

(57) ABSTRACT

A total facet arthroplasty system and method of assembling a longitudinal member therein comprises a first pedicle screw assembly configured in a monoaxial position, wherein the first pedicle screw assembly comprises a first opening; a second pedicle screw assembly configured in a polyaxial position, wherein the second pedicle screw assembly comprises a second opening; and a longitudinal member attaching the first pedicle screw assembly to the second pedicle screw assembly such that the longitudinal member is mounted through the first and second openings, wherein the first opening is positioned in an orientation other than parallel with respect to the second opening. The longitudinal member comprises an angled orientation other than 180° or a whole factor thereof.

8 Claims, 8 Drawing Sheets

FIG. 7

| ATTACHING A FIRST PEDICLE SCREW ASSEMBLY CONFIGURED IN A MONOAXIAL POSITION TO A FIRST AREA OF BONE IN A SPINAL COLUMN, WHEREIN THE FIRST PEDICLE SCREW ASSEMBLY COMPRISES A FIRST OPENING. | ~701 |

↓

| ATTACHING A SECOND PEDICLE SCREW ASSEMBLY CONFIGURED IN A POLYAXIAL POSITION TO A SECOND AREA OF BONE IN THE SPINAL COLUMN, WHEREIN THE SECOND PEDICLE SCREW ASSEMBLY COMPRISES A SECOND OPENING. | ~703 |

↓

| ATTACHING A FIRST END OF A LONGITUDINAL MEMBER THROUGH THE FIRST OPENING OF THE FIRST PEDICLE SCREW ASSEMBLY. | ~705 |

↓

| ATTACHING A SECOND END OF THE LONGITUDINAL MEMBER THROUGH THE SECOND OPENING OF THE SECOND PEDICLE SCREW ASSEMBLY, WHEREIN THE FIRST OPENING IS POSITIONED IN AN ORIENTATION OTHER THAN PARALLEL WITH RESPECT TO THE SECOND OPENING. | ~707 |

PEDICLE DYNAMIC FACET ARTHROPLASTY SYSTEM AND METHOD

CROSS REFERENCE TO RELATED APPLICATION

This application is a continuation-in-part of U.S. patent application Ser. No. 11/045,908 filed Jan. 28, 2005 now U.S. Pat. No. 7,862,594, which claims the benefit of U.S. Provisional Patent Application No. 60/548,543 filed on Feb. 27, 2004, and U.S. Provisional Patent Application No. 60/565,658 filed on Apr. 27, 2004.

BACKGROUND

1. Technical Field

The embodiments herein generally relate to medical devices, and, more particularly, to implantable spinal fixation systems.

2. Description of the Related Art

The spinal column is a highly flexible structure comprising bones and connective tissue. While, the spine is capable of multiple degrees of motion, spinal injuries or anatomical irregularities may result in spinal pathologies which limit this range of motion. Orthopedic surgeons often aim to correct spinal irregularities and restore stability to traumatized levels through immobilization of spinal elements. Several conventional spinal implant stabilization systems such as spinal cross-connectors exist to assist doctors in immobilizing the spine. These conventional systems often include components having connective structures such as elongated rods which are positioned on opposite sides of the portion of the spinal column intended to be immobilized and are usually implemented with screws and hooks to facilitate segmental attachment of these connective structures to the posterior surfaces of the spinal laminae, through the pedicles, and into the spinal vertebral bodies. Ideally, these connective components provide the necessary mechanical stability to achieve spinal immobilization.

Examples of total facet arthroplasty systems are described in U.S. Pat. Nos. 6,811,567; 6,974,478; 7,041,136; 7,074,237; 7,087,084; and 7,090,698, the complete disclosures of which, in their entireties, are herein incorporated by reference.

Some of the conventional total facet arthroplasty systems require complicated surgical techniques and typically have multiple, complex components that are difficult to assemble in-situ. Accordingly, there remains a need for a new total facet arthroplasty system capable of being easily used by a surgeon during a spinal surgical procedure.

SUMMARY

In view of the foregoing, an embodiment provides a total facet arthroplasty system comprising a first pedicle screw assembly configured in a monoaxial position, wherein the first pedicle screw assembly comprises a first opening; a second pedicle screw assembly configured in a polyaxial position, wherein the second pedicle screw assembly comprises a second opening; and a longitudinal member attaching the first pedicle screw assembly to the second pedicle screw assembly such that the longitudinal member is mounted through the first and second openings, wherein the first opening is positioned in an orientation other than parallel with respect to the second opening. Preferably, wherein the longitudinal member comprises an angled orientation other than 180° or a whole factor thereof. Additionally, the first pedicle screw assembly preferably comprises a screw head; a fixator component fixable secured to the screw head; and a blocker adapted to retain the longitudinal member in the screw head. Moreover, the screw head of the first pedicle screw assembly preferably comprises the first opening.

Furthermore, the second pedicle screw assembly preferably comprises a screw head comprising an outwardly projecting expandable bulbous end; a fixator component comprising an open-ended semi-spherical pocket configured for receiving the bulbous end of the screw head; and a blocker adapted to retain the longitudinal member in the screw head. Preferably, the screw head of the second pedicle screw assembly comprises the second opening. Moreover, a polyaxial angulation of the second pedicle screw assembly is preferably approximately 25 degrees/side. Additionally, the first pedicle screw assembly, the second pedicle screw assembly, and the longitudinal member may each comprise an outer coating comprising osteogenic material.

Another embodiment provides an apparatus comprising a pair of primary pedicle screw assemblies configured in a monoaxial position, wherein each of the primary pedicle screw assemblies comprise a first opening; a pair of secondary pedicle screw assemblies configured in a polyaxial position, wherein each of the secondary pedicle screw assemblies comprise a second opening; a first longitudinal member attaching a first one of the primary pedicle screw assemblies to a first one of the secondary pedicle screw assemblies such that the first longitudinal member is mounted through a first opening of the first one of the primary pedicle screw assemblies and a second opening of the first one of the secondary pedicle screw assemblies; and a second longitudinal member attaching a second one of the primary pedicle screw assemblies to a second one of the secondary pedicle screw assemblies such that the second longitudinal member is mounted through a first opening of the second one of the primary pedicle screw assemblies and a second opening of the second one of the secondary pedicle screw assemblies, wherein the first openings of the pair of primary pedicle screw assemblies are positioned in an orientation other than parallel with respect to the second openings of the pair of secondary pedicle screw assemblies. Preferably, the first and second longitudinal members each comprise an angled orientation other than 180° or a whole factor thereof. Moreover, each one of the primary pedicle screw assemblies preferably comprises a screw head; a fixator component fixable secured to the screw head; and a blocker adapted to retain the longitudinal member in the screw head.

Preferably, each screw head of the primary pedicle screw assemblies comprises the first opening. Furthermore, each one of the secondary pedicle screw assemblies preferably comprises a screw head comprising an outwardly projecting expandable bulbous end; a fixator component comprising an open-ended semi-spherical pocket configured for receiving the bulbous end of the screw head; and a blocker adapted to retain the first longitudinal member in the screw head. Preferably, each screw head of the secondary pedicle screw assemblies comprises the second opening. Moreover, a polyaxial angulation of each one of the secondary pedicle screw assemblies is preferably approximately 25 degrees/side. Also, the pair of primary pedicle screw assemblies, the pair of secondary pedicle screw assemblies, the first longitudinal member, and the second longitudinal member may each comprise an outer coating comprising osteogenic material.

Another embodiment provides a method of inserting a longitudinal member in a total facet arthroplasty system, wherein the method comprises attaching a first pedicle screw assembly configured in a monoaxial position to a first area of bone in a spinal column, wherein the first pedicle screw assembly comprises a first opening; attaching a second pedicle screw assembly configured in a polyaxial position to a second area of bone in the spinal column, wherein the second pedicle screw assembly comprises a second opening; attaching a first end of the longitudinal member through the first opening of the first pedicle screw assembly; and attaching a second end of the longitudinal member through the second opening of the second pedicle screw assembly, wherein the first opening is positioned in an orientation other than parallel with respect to the second opening. The method may further comprise the longitudinal member configured in an angled orientation other than 180° or a whole factor thereof. Moreover, a polyaxial angulation of the second pedicle screw assembly is preferably approximately 25 degrees/side. Furthermore, the first pedicle screw assembly, the second pedicle screw assembly, and the longitudinal member may each comprise an outer coating comprising osteogenic material.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 7 is a flow diagram illustrating a preferred method according to an embodiment herein.

DETAILED DESCRIPTION OF PREFERRED EMBODIMENTS

Figure 1:
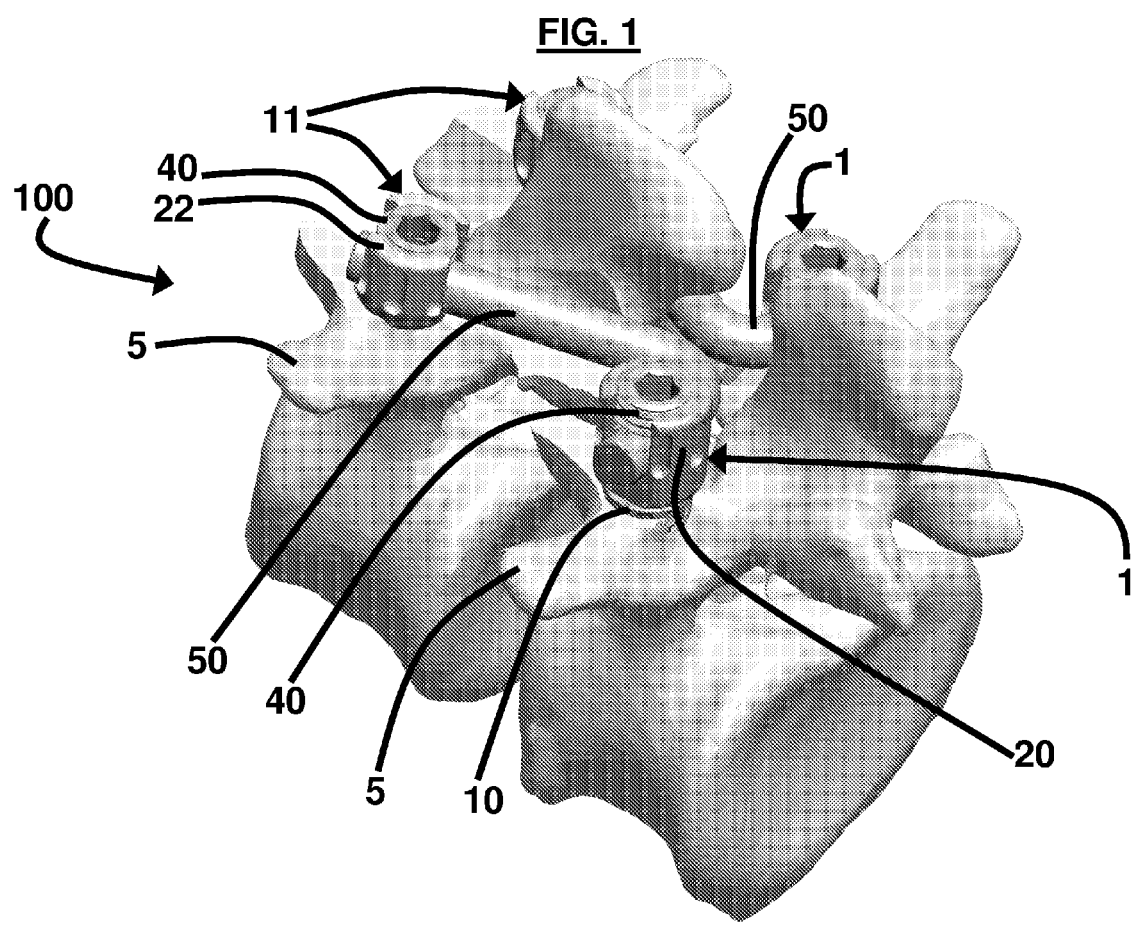
FIG. 1 illustrates an in-situ perspective view of a total facet arthroplasty system according to an embodiment herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a new total facet arthroplasty system capable of being easily used by a surgeon during a spinal surgical procedure. The embodiments herein achieve this by providing a total facet arthroplasty system that retains spine segment motion and approximates natural body biomechanics and includes standard pedicle screw systems that are used for spinal fusion such as those described in U.S. patent application Ser. Nos. 11/045,908; 11/048,189; and 11/048,213, the complete disclosures of which, in their entireties, are herein incorporated by reference, and further includes standard components described in these patent applications, and requires standard surgical techniques and typical time of insertion. Referring now to the drawings, and more particularly to FIGS. 1 through 7, where similar reference characters denote corresponding features consistently throughout the figures, there are shown preferred embodiments.

Figure 5A:
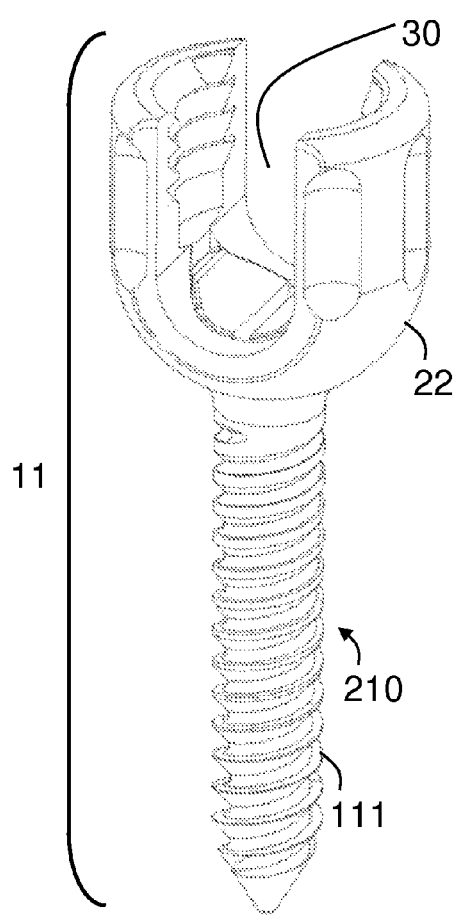
FIGS. 5(A) and 5(B) illustrate schematic views of a monoaxial screw system according to an embodiment herein.
Figure 5B:
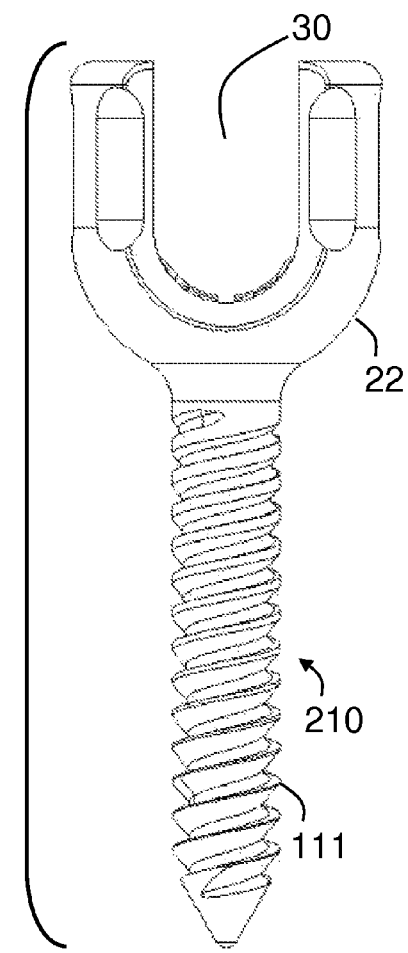
Figure 6A:
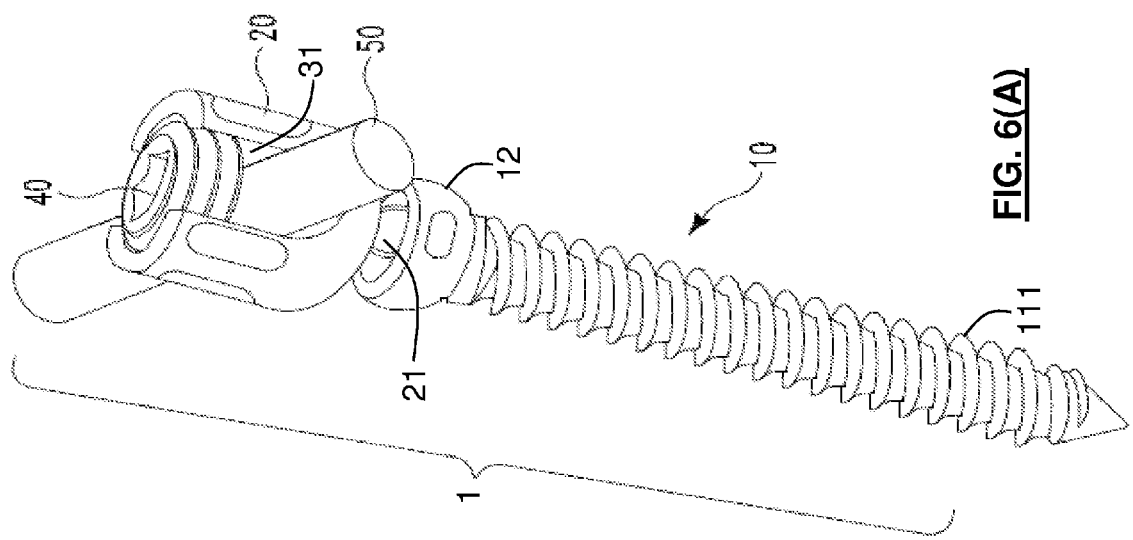
FIGS. 6(A) and 6(B) illustrate schematic views of a polyaxial screw system according to an embodiment herein.
Figure 6B:
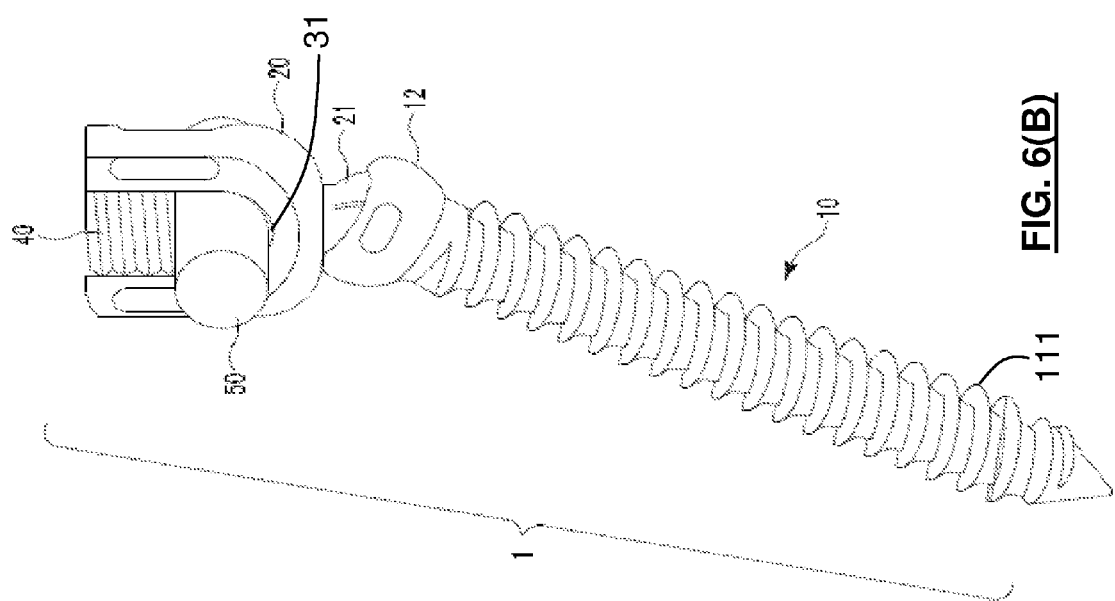

FIGS. 1 through 4 illustrate several views of in-situ total facet arthroplasty system 100 according to an embodiment herein. The system 100 preferably comprises a superior (cephalad) screw system 11, which is preferably embodied as a monoaxial pedicle screw assembly (as shown in FIGS. 5(A) and 5(B)). The system 100 also includes an inferior (caudal) screw system 1, which is preferably embodied as a polyaxial (i.e., dynamic) pedicle screw assembly (as shown in FIGS. 6(A) and 6(B)), such as that described in U.S. patent application Ser. No. 11/045,908, incorporated herein by reference.

The monoaxial screw assembly 11 shown in FIGS. 5(A) and 5(B) comprises a one-piece assembly comprising a screw head 22 fixably attached to a bone screw (fixator component) 210 with a threaded end 111 for engaging a bone 5 (shown in FIGS. 1 through 4). Furthermore, a longitudinal member (not shown in FIGS. 5(A) and 5(B)) is slidably mounted in the opening 30 of the screw head 20 and is retained in place by a set-screw (i.e., blocker) (not shown in FIGS. 5(A) and 5(B)).

The polyaxial screw assembly 1 shown in FIGS. 6(A) and 6(B) comprises a bone screw (fixator component) 10 having a threaded end 111 for engaging a bone 5 (shown in FIGS. 1 through 4) and a concave female socket end 12 for engaging and receiving a outwardly projecting bulbous end 21 of the screw head 20. Furthermore, a longitudinal member 50 is slidably mounted in opening 31 of the screw head 20 and is retained in place by a set-screw (i.e., blocker) 40. Additionally, the longitudinal member 50 is locked in each screw head 20 by the internal set-screw 40 providing fixation at the superior screw system 11 and retaining polyaxial motion at the inferior screw system 1. Preferably, the angulation of the polyaxial screw system 1 is approximately 25 degrees/side.

Figure 2:
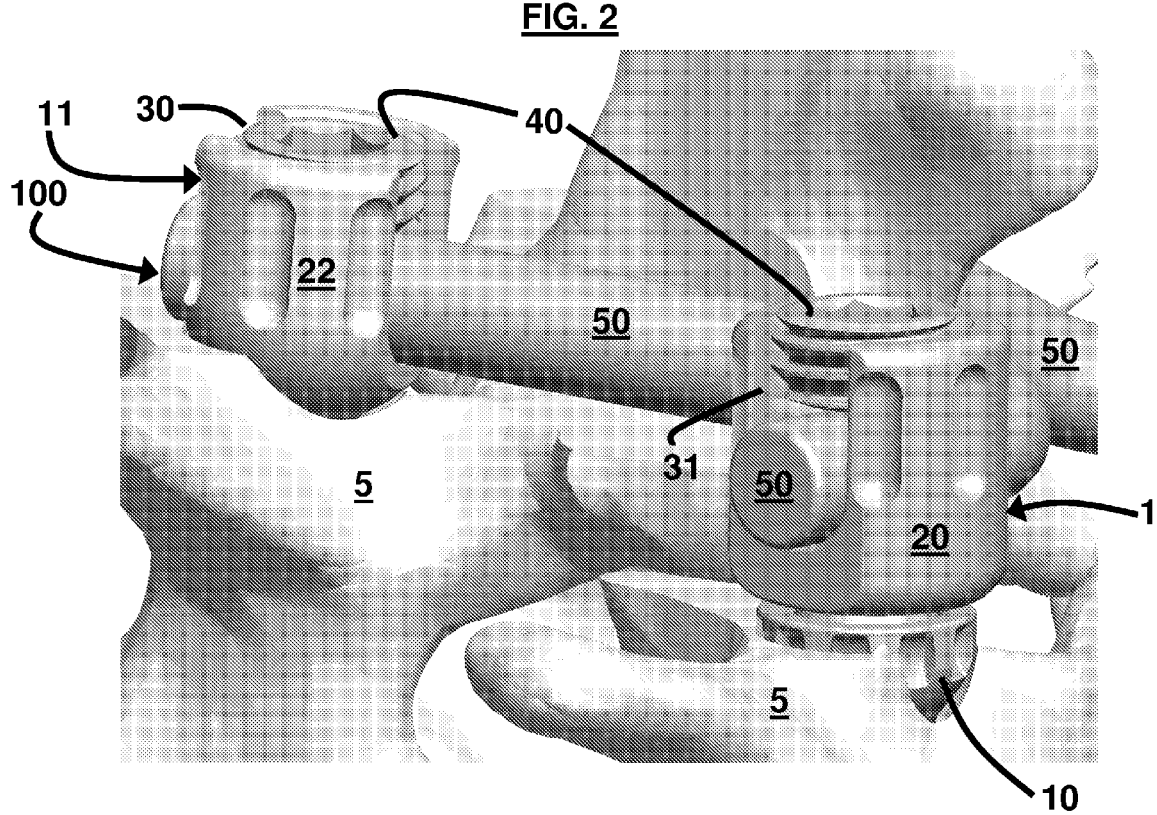
FIG. 2 illustrates an enlarged in-situ perspective view of a total facet arthroplasty system according to an embodiment herein.
Figure 3:
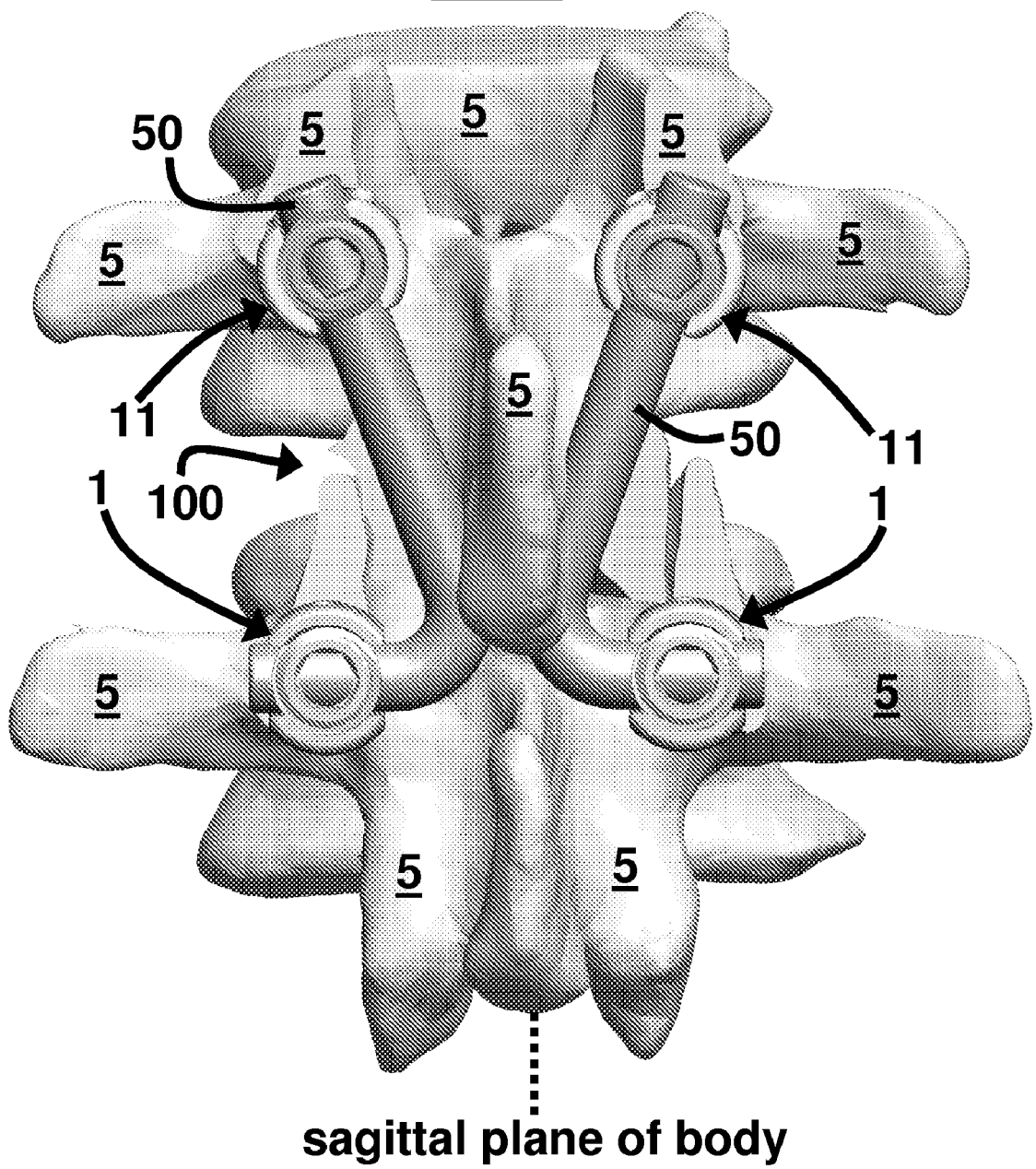
FIG. 3 illustrates an in-situ front view of a total facet arthroplasty system according to an embodiment herein.
Figure 4:
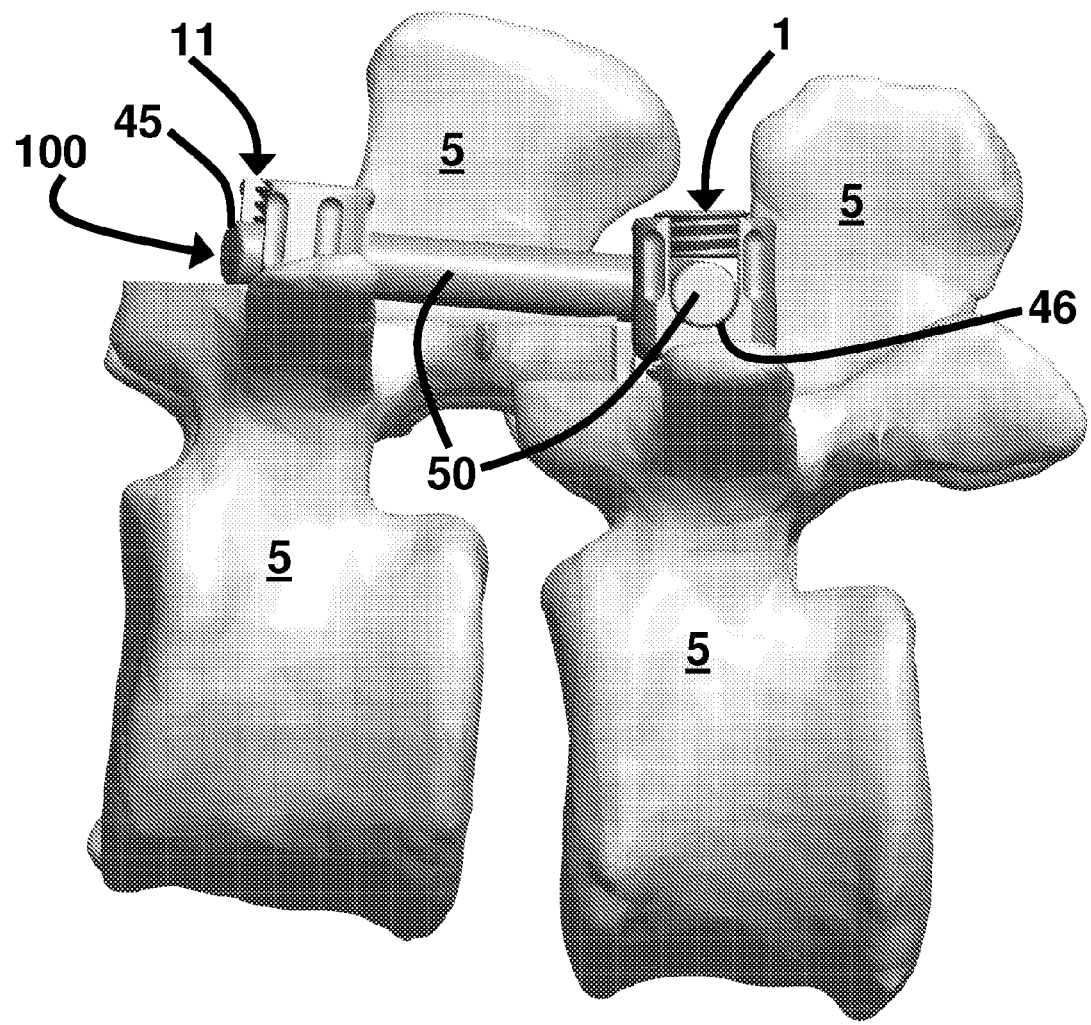
FIG. 4 illustrates an in-situ side view of a total facet arthroplasty system according to an embodiment herein.

Preferably, as best seen in FIGS. 2 and 3, the opening 30 of the superior screw system 11 is positioned slightly offset to parallel to the sagittal plane of the body. Moreover, the opening 31 of the inferior screw head 1 is preferably positioned nearly perpendicular to the sagittal plane. In a preferred embodiment, the longitudinal member 50 is pre-bent in the necessary orientation to link the superior 11 and inferior 1 screw systems together. Furthermore, the longitudinal member 50 can be cut to length at the cephalad 45 and caudal 46 ends to avoid protrusion into soft tissue of the bone 5.

In an alternative embodiment, the superior 11 and inferior 1 screw systems may be any combination of monoaxial or polyaxial pedicle screw assemblies. Additionally, the longitudinal member 50 may be L-shaped with any angle, question mark shaped, or curved with any cross-sectional shape or configuration. The materials for all components may be various grades metal, polymers, or shape-memory materials. Furthermore, the various components may be coated with various wear-resistant materials to provide optimized bearing surfaces. Also, the various components may be coated with osteogenic materials to promote fixation in the bone 5.

FIG. 7, with reference to FIGS. 1 through 6(B), is a flow diagram illustrating a method of inserting a longitudinal member 50 in a total facet arthroplasty system 100, wherein the method comprises attaching (701) a first pedicle screw assembly 11 configured in a monoaxial position to a first area of bone 5 in a spinal column, wherein the first pedicle screw assembly 11 comprises a first opening 30; attaching (703) a second pedicle screw assembly 1 configured in a polyaxial position to a second area of bone 5 in the spinal column, wherein the second pedicle screw assembly 1 comprises a second opening 31; attaching (705) a first end 45 of the longitudinal member 50 through the first opening 30 of the first pedicle screw assembly 11; and attaching (707) a second end 46 of the longitudinal member 50 through the second opening 31 of the second pedicle screw assembly 1, wherein the first opening 30 is positioned in an orientation other than parallel with respect to the second opening 31. The method may further comprise the longitudinal member 50 configured in an angled orientation other than 180° or a whole factor thereof. Moreover, a polyaxial angulation of the second pedicle screw assembly 1 is preferably approximately 25 degrees/side. Furthermore, the first pedicle screw assembly 11, the second pedicle screw assembly 1, and the longitudinal member 50 may each comprise an outer coating comprising osteogenic material.

The embodiments herein generally provides a unilateral or bilateral standalone dynamic facet arthroplasty system 100 that enables the surgeon to perform a full facetectomy but retain the motion and associated constraints provided by the natural facets by transferring the spinal load to the pedicles. The system 100 includes a superior monoaxial pedicle screw system 11 and an inferior polyaxial pedicle screw system 1 linked by a shaped longitudinal member 50. The embodiments herein provide a user-friendly top loading configuration that is comparable to standard pedicle screw systems. The system 100 is implanted via the same surgical techniques for ease of use. Moreover, the system 100 off-loads the natural facets or allows a full facetectomy to decompress nerve roots or alleviate back pain. In addition, the system 100 is easily revisable in case of adverse events. Furthermore, the system 100 can be substituted with standard pedicle screw assemblies enabling spinal fusion which is the current and accepted standard of care. The system 100 can also be used to augment a total disc arthroplasty device (artificial disc) by providing off-loading or further motion constraint if there are concerns of subluxation, subsidence, or vertebral body fracture. Preferably, the embodiments herein are used for total facet arthroplasty or in conjunction with total disc arthroplasty prostheses.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A total facet arthroplasty system comprising:
   a first pedicle screw assembly configured in a monoaxial position, wherein said first pedicle screw assembly comprises a first opening;
   a second pedicle screw assembly configured in a polyaxial position, wherein said second pedicle screw assembly comprises:
      a second opening;
      a screw head comprising an outwardly projecting expandable bulbous end;
      a fixator component comprising an open-ended semi-spherical pocket that receives the bulbous end of said screw head; and
      a blocker that retains said longitudinal member in said screw head; and
   a longitudinal member attaching said first pedicle screw assembly to said second pedicle screw assembly,
   wherein said longitudinal member is mounted through the first and second openings.

2. The total facet arthroplasty system of claim 1, wherein said longitudinal member comprises an angled orientation other than 180° or a whole factor thereof.

3. The total facet arthroplasty system of claim 1, wherein said first pedicle screw assembly comprises:
   a screw head;
   a fixator component fixably secured to said screw head; and
   a blocker that retains said longitudinal member in said screw head.

4. The total facet arthroplasty system of claim 3, wherein said screw head of said first pedicle screw assembly comprises said first opening.

5. The total facet arthroplasty system of claim 1, wherein said second pedicle screw assembly further comprises:
   a screw head slot within said screw head, wherein said screw head slot receives said longitudinal member;
   screw head threading embedded within an interior surface of said screw head slot;
   blocker threading etched on an outer surface of said blocker,
   wherein said blocker threading is configured to mate with said screw head threading.

6. The total facet arthroplasty system of claim 5, wherein said screw head of said second pedicle screw assembly comprises said second opening.

7. The total facet arthroplasty system of claim 1, wherein a polyaxial angulation of said second pedicle screw assembly is approximately 25 degrees/side.

8. The total facet arthroplasty system of claim 1, wherein said first pedicle screw assembly, said second pedicle screw assembly, and said longitudinal member each comprise an outer coating comprising osteogenic material.

* * * * *